(12) United States Patent
Muelleder et al.

(10) Patent No.: US 9,707,560 B2
(45) Date of Patent: Jul. 18, 2017

(54) METHOD FOR FILLING A MICROFLUIDIC DEVICE USING A DISPENSING SYSTEM AND CORRESPONDING TEST SYSTEM

(71) Applicant: Greiner Bio-One GmbH, Kremsmuenster (AT)

(72) Inventors: Oliver Muelleder, Luftenberg (AT); Max Sonnleitner, Linz (AT)

(73) Assignee: Greiner Bio-One GmbH, Kremsmuenster (AT)

( * ) Notice: Subject to any disclaimer, the term of this patent is extended or adjusted under 35 U.S.C. 154(b) by 0 days.

(21) Appl. No.: 14/786,599

(22) PCT Filed: Apr. 23, 2014

(86) PCT No.: PCT/AT2014/050100
§ 371 (c)(1),
(2) Date: Oct. 29, 2015

(87) PCT Pub. No.: WO2014/172740
PCT Pub. Date: Oct. 30, 2014

(65) Prior Publication Data
US 2016/0059232 A1    Mar. 3, 2016

(30) Foreign Application Priority Data

Apr. 25, 2013  (AT) .............................. A 50286/2013

(51) Int. Cl.
*B01L 3/00* (2006.01)
*F04B 19/00* (2006.01)
(Continued)

(52) U.S. Cl.
CPC ......... *B01L 3/50273* (2013.01); *B01L 3/0293* (2013.01); *B01L 3/502715* (2013.01);
(Continued)

(58) Field of Classification Search
CPC ....... G01N 35/1016; G01N 2035/1034; G01N 2035/1041; G01N 2035/1044
See application file for complete search history.

(56) References Cited

U.S. PATENT DOCUMENTS 5,927,547 A * 7/1999 Papen .................. B01L 3/0268
                                                          222/333
6,589,790 B1 * 7/2003 Colin .................... B01L 3/5025
                                                          141/130
(Continued)

FOREIGN PATENT DOCUMENTS

CN        101126765 A      2/2008
CN        101155510 A      4/2008
(Continued)

OTHER PUBLICATIONS

Squires et al: Making it stick: convection, reaction and diffusion in surface-based biosensors, Perspective, nature biotechnology, vol. 26, No. 4, Apr. 2008, pp. 417-426.
(Continued)

*Primary Examiner* — Lisa Caputo
*Assistant Examiner* — Tran M Tran
(74) *Attorney, Agent, or Firm* — Collard & Roe, P.C.

(57) ABSTRACT

The invention relates to a method of filling nozzles (11) of a dispensing system (2) of a test system (1) comprising a dispensing system (2) and a microfluidic device (3) comprising at least the following steps: (a) transporting the solution from the container (6) via the nozzle (11) of the dispensing system (2) to the sample application opening (13) of the microfluidic device (3) by means of a micro-pump (10), (b) further transporting the solution into the measuring region of the microfluidic passage (14) of the microfluidic device (3), (c) measuring a light signal in the measuring region of the microfluidic device (3) by means of at least one photosensitive sensor (4) with a plurality of photodetectors
(Continued)

(5), and (d) deactivating the micro-pump (10) when the light signal and/or a change in the light signal is detected.

18 Claims, 2 Drawing Sheets

(51) Int. Cl.
| | | |
|---|---|---|
| *G01N 21/76* | (2006.01) | |
| *B01L 3/02* | (2006.01) | |
| *G01N 35/10* | (2006.01) | |
| *G01N 1/28* | (2006.01) | |
| *G01N 35/00* | (2006.01) | |

(52) U.S. Cl.
CPC ............ *F04B 19/006* (2013.01); *G01N 1/28* (2013.01); *G01N 21/76* (2013.01); *G01N 35/10* (2013.01); *B01L 2200/0642* (2013.01); *B01L 2200/0689* (2013.01); *B01L 2200/10* (2013.01); *B01L 2200/14* (2013.01); *B01L 2300/0609* (2013.01); *B01L 2300/0645* (2013.01); *B01L 2300/0654* (2013.01); *B01L 2300/0809* (2013.01); *B01L 2300/0851* (2013.01); *B01L 2300/0864* (2013.01); *B01L 2300/123* (2013.01); *B01L 2400/0487* (2013.01); *B01L 2400/0605* (2013.01); *G01N 2035/00158* (2013.01); *G01N 2201/02* (2013.01)

(56) References Cited

U.S. PATENT DOCUMENTS

| | | | | |
|---|---|---|---|---|
| 6,620,625 B2 * | 9/2003 | Wolk | ................ | B01J 19/0046 204/451 |
| 6,878,555 B2 * | 4/2005 | Andersson | ............ | B01F 5/0646 422/506 |
| 7,189,580 B2 * | 3/2007 | Beebe | ................ | B01L 3/50273 137/12 |
| 7,294,309 B1 * | 11/2007 | Goldberg | ............. | B01L 3/0268 222/195 |
| 7,618,590 B2 * | 11/2009 | Gleason | ................ | B01L 3/0268 422/504 |
| 7,625,760 B2 * | 12/2009 | Kitaguchi | ......... | B01L 3/502715 422/562 |
| 8,034,296 B2 | 10/2011 | Cox et al. | | |
| 8,293,521 B2 * | 10/2012 | Hanafusa | .............. | B01L 3/0268 435/286.1 |
| 8,580,194 B2 * | 11/2013 | Sonnleitner | ............ | G01N 21/66 422/52 |
| 8,709,357 B2 * | 4/2014 | Imran | .................. | B01J 19/0093 137/147 |
| 8,758,587 B2 | 6/2014 | Sugiyama et al. | | |
| 9,254,486 B2 * | 2/2016 | Imran | ................. | B01J 19/0093 |
| 2003/0132112 A1 | 7/2003 | Beebe et al. | | |
| 2007/0003447 A1 | 1/2007 | Gleason et al. | | |
| 2007/0086922 A1 * | 4/2007 | Andersson | ............ | B01L 3/0268 422/400 |
| 2008/0311006 A1 * | 12/2008 | Bek | ........................ | B01L 3/0262 422/400 |
| 2009/0104078 A1 * | 4/2009 | Seguin | .................. | B01L 3/0224 422/400 |
| 2010/0221704 A1 | 9/2010 | Hanafusa et al. | | |
| 2010/0286803 A1 | 11/2010 | Tillotson et al. | | |
| 2011/0005606 A1 | 1/2011 | Bartels et al. | | |
| 2012/0282682 A1 | 11/2012 | Walsh et al. | | |
| 2013/0294973 A1 | 11/2013 | Sonnleitner | | |

FOREIGN PATENT DOCUMENTS

| | | |
|---|---|---|
| CN | 101253401 A | 8/2008 |
| CN | 201917521 U | 8/2011 |
| CN | 102435659 A | 5/2012 |
| CN | 102612482 A | 7/2012 |
| EP | 1 895 308 A1 | 3/2008 |
| WO | 03/035538 A1 | 5/2003 |
| WO | 2009/059664 A1 | 5/2009 |
| WO | 2012/080339 A1 | 6/2012 |

OTHER PUBLICATIONS

International Search Report of PCT/AT2014/050100, mailed Sep. 18, 2014.

* cited by examiner

METHOD FOR FILLING A MICROFLUIDIC DEVICE USING A DISPENSING SYSTEM AND CORRESPONDING TEST SYSTEM

CROSS REFERENCE TO RELATED APPLICATIONS

This application is the National Stage of PCT/AT2014/050100 filed on Apr. 23, 2014, which claims priority under 35 U.S.C. §119 of Austrian Application No. A 50286/2013 filed on Apr. 25, 2013, the disclosure of which is incorporated by reference. The international application under PCT article 21(2) was not published in English.

The invention relates to a method of filling nozzles of a dispensing system of a test system, as well as a test system comprising a dispensing system, a microfluidic device and at least one photosensitive sensor with a plurality of photodetectors.

Many point of care test systems used for in vitro diagnostics require various solutions to be manually introduced into a sample vessel. For example, WO 2012/080339 A1 discloses a measuring device, whereby three different reagents within the 10 µl volume range have to be manually and sequentially introduced by drops during the course of running the test. The disadvantage of this manual process of dispensing by drops is that the hands-on time involved in processing the test is very long and ties up personnel. Furthermore, being less robust and offering less reproducibility, this manual dropping process poses a certain amount of risk that the results will be distorted. WO 2012/080339 A1 also discloses a device for dispensing reagents in the form of a blister pack.

Automatic dispensing devices solve the problems of manually dispensing reagents. They enable different volumes to be introduced into a sample vessel quickly and accurately. The systems often used for in vitro diagnostics enable volumes in the microliter to nanoliter range to be dispensed with a high degree of precision without contact.

However, conventional dispensing systems for several reagents require expensive and complicated components which are unsuitable for point of care systems.

In the case of conventional automatic dispensing systems with only one nozzle with one outlet orifice and several valves (as well as multiple passages) providing a passage for the requisite reagent, dead volumes remain in the flow path where the reagents mix. This requires complete rinsing after every reagent and the rinsing fluid is collected in a separate container. However, providing a separate fluid circuit for rinsing the nozzles is problematic in a point of care system.

If it is necessary to ensure that the liquids to be dispensed do not come into contact, especially prior to dispensing, because biochemical reactions could otherwise take place in the fluidic system instead of in the measuring chamber, separate fluidic paths have to be provided. For such systems, it is particularly important to ensure that there is no air in the fluidic path prior to dispensing which might affect the quantity of reagent dispensed.

Accordingly, the objective of this invention is to ensure that the fluidic path is completely filled with reagent as far as the outlet orifice before the start of the actual measuring operation.

The objective of the invention is achieved, independently in each case, by a method of filling nozzles of a dispensing system of a test system comprising a dispensing system and a microfluidic device, which microfluidic device comprises at least one sample application opening and a microfluidic passage in which a measuring region is disposed, and the sample application opening is connected to the microfluidic passage, and the dispensing system comprises at least one container with at least one reservoir containing a solution, and the container is connected via a fluid line having at least one micro-pump, after which at least one nozzle is provided as a means of dispensing the solution into the sample application opening of the microfluidic device, comprising at least the steps transporting the solution from the container via the nozzle of the dispensing system to the sample application opening of the microfluidic device by means of the micro-pump, further transporting the solution into the measuring region of the microfluidic passage of the microfluidic device, measuring a light signal in the measuring region of the microfluidic device by means of at least one photosensitive sensor with a plurality of photodetectors, and deactivating the micro-pump when the light signal is detected and/or changes, and a test system comprising at least one dispensing system, a microfluidic device and at least one photosensitive sensor with a plurality of photodetectors which microfluidic device comprises a sample application opening and a microfluidic passage in which a measuring region is disposed, and the sample application opening is connected to the microfluidic passage, and the microfluidic device is detachably disposed in a holder device of the test system so that the measuring region is disposed above the photodetectors of the photosensitive sensor, and the dispensing system comprises at least one container with at least one reservoir containing a solution, and the container is connected via a fluid line to at least one micro-pump, after which at least one nozzle is provided as a means of dispensing the solution into the sample application opening of the microfluidic device.

The advantage of this is that it ensures that a solution is disposed in the nozzle and the correct volume of solution can therefore be dispensed from this nozzle for subsequent method steps without having to fill, rinse or wash the nozzle again, etc.

Based on another embodiment, the dispensing system comprises at least two containers containing solutions, and the first container contains a first solution, in particular a chemiluminescent solution, and the second container contains another solution, preferably an enzyme solution, and the containers are connected via a fluid line to at least one micro-pump, after which at least two nozzles are provided, and a first nozzle is provided as a means of dispensing the first solution, in particular the chemiluminescent solution, and the second nozzle is provided as a means of dispensing the other solution, preferably the enzyme solution, into the sample application opening of the microfluidic device, comprising at least the steps:

transporting the first solution, in particular the chemiluminescent solution, and the other solution, in particular the enzyme solution, from the respective container via the respective nozzle of the dispensing system to the sample application opening of the microfluidic device by means of the at least one micro-pump, measuring a light signal, in particular a chemiluminescence signal, by reacting the first solution, in particular the chemiluminescent solution, and the other solution, in particular the enzyme solution, in the measuring region of the microfluidic device by means of at least one photosensitive sensor with a plurality of photo detectors, and deactivating the at least one micro-pump when the light signal, in particular the chemiluminescence signal, is detected.

If a light signal can be detected in the microfluidic passage, it means that the first solution, in particular the chemiluminescent solution, and the other solution, preferably the enzyme solution, have reacted with one another because the signal is not generated unless the two reagents have reacted with one another. Since there is no contact and hence a reaction of the two solutions is not possible until after they have been dispensed from the respective nozzles, both the first solution, in particular the chemiluminescent solution, and the other solution, preferably the enzyme solution, must therefore have passed through the nozzles. Detection of the light signal generated by the chemical or biochemical reaction of the two reagents is a guarantee that both the first solution, in particular the chemiluminescent solution, and the other solution, preferably the enzyme solution, have reached the measuring region of the microfluidic passage and hence are also present in the nozzles of the dispensing system which transports the liquids to the microfluidic device via the sample application opening. In this respect, it can advantageously be guaranteed that both the nozzle for dispensing the first solution, in particular the chemiluminescent solution, and the nozzle for the other solution, preferably the enzyme solution, have been filled as far as the outlet end with the respective liquid and that the respective correct volume set via the dispensing device will be dispensed on dispensing. In order to carry out various tests with the test system, it is important to ensure, prior to the measurement, that the liquid meniscus in the dispensing device is sitting at the end of the injection nozzles. If the meniscus of the first solution, in particular the chemiluminescent solution, and the other solution, preferably the enzyme solution, were further back in the fluid passage of the nozzle, the corresponding quantity of respective solution would be lacking during the measuring operation leading to distorted results when testing with the test system due to the fact that not enough liquid volume was dispensed. Another advantage is that this also offers a cost-effective system with a high degree of reproducibility. The disadvantage of having to use an additional container for rinsing the fluidic paths as is the case with the prior art is also eliminated by the method proposed by the invention and test system proposed by the invention. Providing a check that the nozzles have been filled right to the end of the outlet orifice also requires no additional sensors which would render a compact design of a point of care system impossible.

Based on another embodiment,
(a) the first solution, in particular the chemiluminescent solution, is transported via the first nozzle to the sample application opening of the microfluidic device by means of the at least one micro-pump and is then sucked into the measuring region of the microfluidic device,
(b) a measurement of the light signal is taken in the measuring region of the microfluidic device by means of at least one photosensitive sensor with a plurality of photodetectors,
(c) the micro-pump is deactivated when the light signal changes, in particular is intensified, due to the optofluidic lens effect,
(d) the other solution, in particular the enzyme solution, is transported via the other nozzle to the sample application opening of the microfluidic device by means of the micro-pump and is then sucked into the measuring region of the microfluidic device,
(e) the light signal, in particular the chemiluminescence signal, in the measuring region of the microfluidic device is detected by means of the photosensitive sensor with a plurality of photodetectors,
(f) the micro-pump is deactivated when the light signal, in particular the chemiluminescence signal, is detected.

The advantage of introducing the solutions sequentially is that the presence of the first solution, in particular the chemiluminescent solution, can be checked independently of the other solution, preferably the enzyme solution. Accordingly, if there is no light signal, in particular a chemiluminescence signal, the source of the error can be pinpointed rapidly, namely either no or too little of the first solution, in particular the chemiluminescent solution, or no or too little of the other solution, preferably the enzyme solution, was dispensed via the nozzle into the sample application opening.

As soon as the first solution is transported into the microfluidic passage, the light signal is changed due to an optofluidic lens effect, in particular is intensified, thereby enabling the meniscus of the first solution to be measured.

Based on another embodiment, other steps are implemented, whereby
(g) an additional solution, in particular a washing solution, is transported via another nozzle to the sample application opening of the microfluidic device by means of the micro-pump and is then sucked into the measuring region of the microfluidic device,
(h) the shift of the previously measured light signal, in particular the chemiluminescence signal, in the measuring region of the microfluidic device is measured by means of at least one photosensitive sensor with a plurality of photodetectors,
(i) the micro-pump is deactivated on detection of the light signal shift.

This means that it is also possible to guarantee that the nozzle has been filled with the additional solution, in particular the washing solution, prior to dispensing the additional solution during the actual test in the test system.

Contact of the solutions, in particular the enzyme solution, with air can cause the outlet orifice of the nozzle to become blocked. However, the outlet orifices of the nozzles can also dry out, as a result of which the liquid meniscus recedes therein and an incorrect sample volume is dispensed during the next test. This being the case, the outlet orifices of the nozzles are closed off by means of at least one sealing device, in particular one which is airtight, after the micro-pump has been deactivated.

The advantage of the micro-pump combined with the nozzle is that a stream of nanoliter drops of the respective liquid is generated, thereby enabling targeted dispensing of the respective solution from the outlet orifice of the nozzle into the sample application opening of the microfluidic device without contact. Targeted dispensing is necessary in order to ensure that the entire volume of the respective solution is also actually dispensed into the sample application opening of the microfluidic device to obtain a correct test result. Due to the micro-pump, a few microliters can be dispensed through the sample application opening of the microfluidic device with an accuracy of ±1 µl.

Once the nozzles of the dispensing system have been filled, a biological sample is placed in the sample application opening and transported through the microfluidic passage where target molecules of the biological sample react via specific binding sites with molecules disposed in the test sections of the measuring regions, and when the solutions from the dispensing system are added, a chemical or biochemical reaction takes place causing light to be emitted and generating a light signal which is detected by the photosensitive sensor with a plurality of photodetectors, thereby enabling a rapid evaluation of the biological sample to be made because several samples can be measured one after the other without the need for rinsing in between.

Furthermore, based on another embodiment, the dispensing system may comprise at least two containers containing solutions, in which case the first container contains a first solution, in particular a chemiluminescent solution, and the second container contains another solution, preferably an enzyme solution, and the containers are connected via a fluid line to at least one micro-pump, after which at least two nozzles are provided, and a first nozzle is used to dispense the first solution, in particular the chemiluminescent solution, and the second nozzle is used to dispense the other solution, preferably the enzyme solution, into the sample application opening of the microfluidic device, thereby enabling rapid priming of the test system.

Based on another embodiment, the containers have an interface with a port to provide a connection to a standard luer cone of the fluid line in order to establish a disconnectable connection of the containers via the fluid line to the micro-pump. This enables the containers to be docked without the inclusion of air. Also of advantage is the fact that empty containers can be easily replaced with full containers as soon as a solution contained therein has been used without introducing air into the fluidic path of the dispensing system.

If the containers constituting a reservoir for the respective solutions are provided in the form of collapsible bags, the inclusion of air bubbles into the dispensing system, in particular into the nozzles, is also prevented. Accordingly, this also obviates the need to vent the container.

Based on another embodiment, at least one check valve is disposed in the fluid line between the container and micro-pump, in particular with biasing means. The check valve blocks any backflow of liquid to the reservoir of the container. Due to the biased arrangement, any over-pressure which might prevail in the reservoir of the container is damped, thereby preventing liquid from dripping out of the outlet orifice of the nozzle into the sample application opening of the microfluidic device.

Furthermore, at least one sealing device is disposed in the region of an outlet orifice of the nozzles so that the outlet orifice of the nozzle can be closed, thereby preventing both the liquid meniscus from receding and any blockage of the outlet orifice of the nozzles. Especially between measurements, the nozzles can be closed in an airtight arrangement, thereby preventing blockages in the nozzles.

The dispensing system comprises at least two dispenser units, and the first dispenser unit contains a container with a first solution, in particular a chemiluminescent solution, which is connected via a fluid line to at least one micro-pump and then to a nozzle, and the second dispenser unit contains a container with another solution, in particular an enzyme solution, which is likewise connected via a fluid line to at least one micro-pump and then to a nozzle, and optionally the third dispenser unit contains a container with an additional solution, in particular a washing solution, which is likewise connected via a fluid line to at least one micro-pump and then to a nozzle. It has proved to be of advantage to opt for a parallel arrangement of at least two dispenser units because this means that there are totally separate fluidic paths in the dispensing system which cannot come into contact with one another until the transition to the microfluidic device and any premature reaction or contamination of one solution with another can therefore be prevented.

In each dispenser unit, an interface may be provided on the container with a port to provide a connection to a standard luer cone and at least one check valve is provided in the fluid line between the container and micro-pump, in particular with biasing means, which on the one hand enables the containers to be easily removed from the rest of the test system, in particular the dispensing system, and on the other hand enables damping of an over-pressure of the container to prevent any dripping onto the sample application opening of the microfluidic device as well as preventing any backflow of the solution into the container.

The nozzles of adjacent dispenser units are preferably disposed so that they dispense nanoliter drops of the solutions into the same sample application opening of the microfluidic device. The advantage of this is that additional devices or features to direct the stream of liquid to the sample application opening are obsolete.

It has also proved to be of advantage if an outlet end of a nozzle is disposed at a distance of 0.1 mm to 80 mm from the sample application opening of the microfluidic device, as a result of which a distance between the dispensing device and microfluidic device is overcome, thereby enabling the respective solution to be dispensed into the sample application opening of the microfluidic device without contact. This prevents the solutions from different dispenser units or nozzles from contaminating one another.

To provide a clearer understanding, the invention will be described in more detail below with reference to the appended drawings.

These are highly schematic, simplified diagrams illustrating the following:

FIG. 1 a schematic diagram of the test system;

FIG. 2 a diagram of signal amplification by the optofluidic effect;

FIG. 3 a diagram of the chemiluminescence signal in the measuring region of the microfluidic passage;

FIG. 4 a diagram of the shift of the chemiluminescence signal in the measuring region of the microfluidic passage.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

All the figures relating to ranges of values in the description should be construed as meaning that they include any and all part-ranges, in which case, for example, the range of 1 to 10 should be understood as including all part-ranges starting from the lower limit of 1 to the upper limit of 10, i.e. all part-ranges starting with a lower limit of 1 or more and ending with an upper limit of 10 or less, e.g. 1 to 1.7, or 3.2 to 8.1 or 5.5 to 10.

This invention describes a method of preparing a test system for use in in-vitro diagnostics, in particular in the point of care (POC) sector, as well as the test system.

FIG. 1 is a schematic diagram in section illustrating the test system 1 proposed by the invention, which comprises at least one dispensing system 2, a microfluidic device 3 and a photosensitive sensor 4 with a plurality of photodetectors 5. The test system 1 is controlled by control modules.

Also illustrated are a container 6 with a bag 7, an interface 8, a check valve 9, a micro-pump 10 and a nozzle 11 of the dispensing system 2, which are connected to one another via a fluid line 12.

The microfluidic device 3 comprises, next to the sample application opening 13, a microfluidic passage 14 incorporating the measuring region having several test sections and optionally a reservoir 15. The microfluidic device 3 is retained in a holder device 16 on or in which the photosensitive sensor 4 is disposed.

Due to the reaction of the sample material transported in the microfluidic device 3 with the reagents from the dispensing system 2 or the reagents of the dispensing system 2 themselves, a change in optical property or a chemical or biochemical reaction based on a light emission occurs in the test sections so that the photodetectors 5 cooperating with the respective test section detect a change in the incident light intensity.

The light emission or change to the light signal may be based on a chemical or biochemical reaction in the case of chemiluminescence or a color change for example, or alternatively, in the case of fluorescence or phosphorescence, on the application of excitation energy from other sources. It is preferable if a chemiluminescence signal is detected.

In one possible embodiment, the dispensing system 2 is made up of a container 6 with a reservoir for a solution. A fluid line 12 connects the container 6 to the micro-pump 10 and then to the nozzle 11.

The dispensing system 2 preferably comprises at least two containers 6 which are connected respectively via a fluid line 12 to a micro-pump 10 and at least two nozzles 11. The dispensing system 2 may also comprise several dispenser units 17, in which case a dispenser unit 17 comprises at least one container 6, a fluid line 12, a micro-pump 10 and a nozzle 11. The nozzle 11 of a dispenser unit 17 can be closed by means of a sealing device 18.

The containers 6 serve as reservoirs for the different solutions. Based on one possible embodiment, they are provided in the form of collapsible bags 7 of the type known from intravenous therapy, as a result of which no air bubbles can get into the fluidic path of the dispensing system 2. The chemiluminescent solution is preferably contained in one bag 7 and the enzyme solution in another bag 7 and the washing solution in an additional bag 7. However, other solutions may also be disposed in the containers 6, for example of the type needed for a color reaction.

The collapsible bag 7 and fluid line 12, provided in the form of a hose system, are connected to one another at an interface 8. The interface 8 in this instance forms a luer connection. At their bottom end, the collapsible bags 7 have a luer cone, which establishes a fluid-tight and airtight connection to the fluid line 12. The seal is obtained by the conical construction of the connecting parts, the so-called luer cone. The container 6 incorporating the reservoir can be easily changed by means of the luer connection without air being included.

Several of these bags 7 can be grouped in a housing to form a separate unit. This unit can be easily detached from the rest of the dispensing system 2 via the interface 8, for example once a specific number of tests have been carried out with the test system 1 and the volume of liquids contained in the bags 7 has been used. How often such a unit has been used and hence when it needs to be replaced can be evaluated by means of an RFID system, for example.

The micro-pump 10 enables the smallest of volumes to be conveyed. It comprises injection-cast parts for the housing and pump chamber, a piezo actuator and valves. Such micro-pumps 10 are known from the prior art, for example as sold by Bartels-Mikrotechnik and described in WO2009/059664 A1.

The fluidic path for the solutions starts in the respective liquid reservoir in the container 6 and extends via the fluid line 12 to the micro-pump 10, terminating in the respective nozzle 11. The micro-pump 10 in combination with the nozzle 11 generates a stream of nanoliter drops, enabling a few microliters to be dispensed selectively and without contact to the sample application opening 13 of the microfluidic device 3. The nanoliter drops are droplets with a volume of 1 nl to 100 nl, preferably 2 nl to 10 nl, in particular 5 nl.

In the region of the outlet end or outlet orifice, the nozzles 11 have a diameter of less than 500 μm. Preferably, the diameter of the nozzle 11 in this region is between 100 μm and 300 μm, in particular 250 μm.

Based on a preferred embodiment, a check valve 9 is disposed in the fluidic path between the micro-pump 10 and container 6, which blocks any backflow of the respective solution to the reservoir of the container 6. In addition, a check valve 9 may be fitted in a biased arrangement, in which case the biasing action compensates for an overpressure of the reservoir and thus prevents subsequent dripping out of the nozzles 11 into the sample application opening 13 of the microfluidic device 3.

Based on another embodiment of the invention, a sealing device 18 may also be provided, which closes the nozzles 11 to make them airtight between measurements and thus prevents blockages in the nozzles 11 in the region of the outlet orifice of the nozzles 11. The sealing device 18 may be provided separately for each nozzle 11 or may be provided for only selected nozzles 11. In an alternative embodiment, the sealing device 18 may also be designed as one piece serving several nozzles 11, for example in the form of a silicone pad.

A bag 7 with an interface 8 to the fluid line 12 incorporating a biased check valve 9 and a micro-pump 10 in combination with a nozzle 11 form a dispenser unit 17 of a dispensing system 2.

Several such dispenser units 17 may be disposed in a parallel arrangement in the dispensing system 2. In a preferred embodiment, three dispenser units 17 are disposed adjacent to one another, the dispenser units 17 being different due to the solutions contained in the reservoir of the bag 7. Disposed in a first bag 7 is a solution responsible or necessary for the chemical or biochemical reaction, in particular a chemiluminescent solution, a second bag 7 contains the other solution, preferably an enzyme solution, and a third bag 7 contains the additional solution, in particular a washing solution. So that they meet at the same sample application opening 13 of the microfluidic device 3 when using three adjacent nozzles 11, the two outer nozzles 11 are disposed at an acute angle with respect to the middle nozzle 11.

In an alternative embodiment, the dispensing system 2 may also comprise only one dispenser unit 17, in which case it will have several bags 7, each with a fluid line 12 leading to a micro-pump 10 with several chambers for the different solutions, from where the respective solutions are transported via mutually separate nozzles 11.

In order to ensure that the respective solution is correctly dispensed into the sample application opening 13 of the microfluidic device 3, the outlet orifice of the nozzle 11 is disposed at a distance of 0.1 mm to 80 mm from the sample application opening 13, preferably at a distance of 1 mm to 50 mm, and in particular at a distance of 2 mm to 20 mm.

The microfluidic device 3 comprises at least one sample application opening 13, a microfluidic passage 14 and a reservoir 15. The microfluidic passage 14 has a length of 30 mm to 50 mm, a width of 1 mm to 4 mm and a height of 10 μm to 200 μm and can be produced by injection casting. It is preferable if the passage has a length of 40 mm, a width of 2 mm and a height of 100 μm. The measuring region is disposed in the microfluidic passage 14, where molecules having specific binding sites for the specific target molecules of a biological sample are also immobilized. Due to the geometric nature of the microfluidic passage 14, the liquid moves from the sample application opening 13 through the microfluidic passage 14 as far as the reservoir 15 by capillary action. Once a sample has been dispensed into the sample application opening 13, a pressure gradient builds up in the passage 14, resulting in a capillary force in the direction of the reservoir 15, thereby guaranteeing an automatic passage for the sample through the passage or microfluidic system, i.e. no additional means are needed to generate a pressure difference or flow movement. In particular, what takes place is a so-called convection-driven hybridization whereby convection gradients build in the passage 14 which, in addition to transporting the sample through the passage 14, also direct the sample material to the test sections of the measuring region (Squires T M et al., "Making it stick: convection, reaction and diffusion in surface-based biosensor", Nature Biotech, 26, 4, 2008). When a test is being conducted, the analytes in the biological sample come into contact with the molecules immobilized in the measuring region, causing a chemical binding reaction in the respective measuring region in the presence of a corresponding analyte in the sample, which then results in a chemical or biochemical reaction once the corresponding reagents are added (e.g. chemiluminescence, color change, etc.) involving a light emission.

Other design options for the microfluidic device 3 with a view to directing more light onto the photosensitive sensor 4 include making the boundary surface of the passage 14 lying opposite the photosensitive sensor 4 optically reflective; providing the passage 14 with a concave cross-section which will serve as a collector lens; fitting a light deflector structure in the microfluidic device 3; designing the microfluidic device 3 as an optical fiber plate. Details of the respective design options for the microfluidic device 3 are described in WO 2012/080339 and constitute part of the disclosure of this invention.

In an alternative embodiment, the microfluidic passage 14 may also be filled by means of a pump, preferably a micro-pump. In the case of a microfluidic device 3 of this type, no reservoir causing a capillary action is necessary.

The microfluidic device 3 is detachably retained in or on a holder device 16 so that the light outlet end of the microfluidic device 3 faces the photosensitive sensor 4. The photosensitive sensor 4 is disposed in a main body, and the individual photodetectors 5 are covered by a transparent cover layer. Disposed in the measuring region of the microfluidic device 3 is a plurality of test sections. During the test, the test sections are directed towards a volume of the microfluidic system so that when a sample to be analyzed is introduced into the sample application opening 13 the analyte is subjected to a capillary movement. As a result, the analyte also comes into contact with the test sections in the measuring region.

The microfluidic device 3 is positioned on a holder device 16 in the housing in which the test system 1 is at least partially contained, which is designed so that the microfluidic device 3 is inserted in a stationary part of the holder device 16 and is retained in a fixed arrangement by a second moving and/or folding part of the holder device 16. Another option is to provide a biased element for a part of the holder device 16 which is compressed when the microfluidic device 3 is inserted and thus secures the microfluidic device 3 in the holder device 16. The holder device 16 may also be of a tray type design, in which case the tray is extracted from the housing by operating an element so that the microfluidic device 3 can be placed on it and secured and is then retracted again, and the photosensitive sensor 4 with the photodetectors 5 may already be disposed in the tray element.

The photosensitive sensor 4 with a plurality of photodetectors 5 is disposed so that once the microfluidic device 3 has been positioned and secured in the holder device 16, the test sections in the measuring region of the microfluidic passage 14 lie with their light outlet end above the photodetectors 5 of the photosensitive sensor 4. To this end, the holder device 16 may have a stationary and a longitudinally displaceable, spring-biased retaining part, for example, so that when the microfluidic device 3 is inserted, the moving part can be moved in a longitudinal direction to make it easier to insert the microfluidic device 3 and then secure it accordingly after springing back into the retaining position. In addition to a longitudinally displaceable design, however, another option would be a folding or snap-in mechanism. It would also be possible to provide a pressing element in at least one of the retaining parts, for example a rubber or spring element which secures the microfluidic device 3 in the manner described above once it has been inserted.

The test system 1 is at least partially disposed in a housing and the containers 6 of the dispensing system 2, which need to be readily accessible in order to change them, may also be disposed outside the housing. The housing must provide a lightproof closure of the microfluidic device 3 from the ambient environment. A feeding device for applying the sample may be disposed in the housing which enables it to be transported to the sample application opening 13 of the microfluidic device 3.

The holder device 16 is of a tray type design and transports the microfluidic device 3 into the housing in order to prime it. The photosensitive sensor 4 with the plurality of photodetectors 5 may also be contained in the tray element. A seal element closes the microfluidic device 3 and photosensitive sensor 4 off from the environment in a lightproof arrangement. The seal element may be provided in the form of a groove-spring connection, for example. However, the seal element may also be provided in the form of an elastically deformable element, for example a foamed material or a rubber seal, so that when the tray element is closed causing the seal element to be compressed, the interior of the measuring device is screened off from the environment in a lightproof arrangement. In order to move a biological sample to the sample application opening 13 of the microfluidic device 3 after priming, the tray element is extracted again.

Accordingly, the microfluidic device 3 can be placed in the holder device 16 and the tray element then closed without any sample material or sample chemical being disposed in the microfluidic system already, which ensures that no chemical reaction can be initiated in the test sections of the measuring region. It is not until the tray element has been closed and reliably established a lightproof closure of the microfluidic device 3 that priming takes place and the measurements needed for this purpose are taken. After priming, the biological sample is then introduced, for which purpose the tray element is firstly opened and then the tray element is closed again to make it lightproof for the at least one measurement to be taken with the photosensitive sensor 4 having a plurality of photodetectors 5.

An illuminating device may also be provided in the housing, e.g. LEDs. Other possible explanations about the holder device 16 and illuminating device as well as an explanation of the measuring arrangement comprising the photosensitive sensor 4 with the plurality of photodetectors 5 may be found in WO 2012/080339 and are included in the disclosure of this invention.

In order to keep potential sources of error due to manual actions and personnel costs and hence the overall cost of a test to a minimum, the method by which the test system is operated should be automated as far as possible. After manually adding the sample material, in other words the biological sample to be analyzed, the solutions needed for the test are dispensed into the sample application opening 13 of the microfluidic device 3. However, this is problematic insofar as the volume to be dispensed must be kept as accurate as possible on the one hand and the sequence in which the solutions used for the test are dispensed is accurately predefined on the other hand.

Using the method proposed by the invention, the test is automated to the degree that only the sample to be analyzed has to be introduced manually.

By means of the method of priming of the test system 1 proposed by the invention, changes in the light signal and/or the light emission of chemical or biochemical reactions are measured and their results used as parameters for controlling the process of filling the dispensing system 2.

The microfluidic device 3 needed for the respective test is inserted in the test system 1, in particular on the holder device 16 provided for this purpose. The dispensing system 2 must then be prepared accordingly in order to dispense the reagents needed for the test in the correct volume, free of air bubbles and in the correct sequence. To this end, the preparation or priming may be initiated by a control unit. Alternatively, the preparation may be initiated automatically as soon as the test system 1 detects that a microfluidic device 3 has been fitted in the test system 1 and is also closed in a lightproof arrangement.

In the case of the most basic embodiment, a solution is transported from the container 6 via the nozzle 11 of the dispensing system 2 to the sample application opening 13 of the microfluidic device 3 by means of a micro-pump 10 and then transported on into the measuring region of the microfluidic passage 14 of the microfluidic device 3. In the measuring region of the microfluidic device 3, a measurement is taken of a light signal by means of at least one photosensitive sensor 4 with a plurality of photodetectors 5, and changes in the light signal and/or the light emission of chemical or biochemical reactions are measured. As soon as a light signal or a change in the light signal is detected, the micro-pump 10 is deactivated.

To prepare or prime the test system, the micro-pump 10 is activated in order to transport a first solution, by means of which a chemical or biochemical reaction with another solution makes a light emission possible, out of the first container 6 via the fluidic path comprising at least one hose line, a micro-pump 10 and a nozzle 11 to the sample application opening 13 of the microfluidic device 3. At the same time or subsequently, the other solution, preferably an enzyme solution, is transported out of the second container 6 via another fluidic path likewise to the sample application opening 13. This results in the reaction of the first solution, in particular the chemiluminescent solution, with the other solution, preferably an enzyme solution, and a light signal, in particular a chemiluminescence signal, is generated which can be detected as soon as the liquid is disposed in the measuring region of the microfluidic passage 14. This ensures that both the first solution, in particular the chemiluminescent solution, and the other solution, preferably an enzyme solution, are disposed in the nozzles 11 of the dispensing system 2 and these are therefore filled and ready for the next test.

Based on an alternative embodiment, in order to prepare or prime the test system 1, the first solution, in particular the chemiluminescent solution, can be transported out of the first bag 7 via the fluid line 12 and via the check valve 9 by the micro-pump 10 to the first nozzle 11 and from there dispensed in the form of nanoliter drops into the sample application opening 13 of the microfluidic device 3, in order to be transported from there through the measuring region to the reservoir 15 by capillary action. To this end, the micro-pump 10 is activated first of all and a measurement is taken in the measuring region of the microfluidic passage 14. During the measurement, a change in the signal occurs or a predefined threshold value is exceeded immediately in the presence of a liquid meniscus when there is a solution in the microfluidic passage 14 and the micro-pump 10 is deactivated because the first solution, in the particular chemiluminescent solution, is disposed in the outlet orifice of the first nozzle 11. In order to measure the change in the light signal, a light source may be provided in the test system 1, in particular LEDs. The first solution is preferably transparent. Due to the shape of the microfluidic passage 14 and the refractive index of the liquid, the light signal emitted by a light source when transparent liquid is in the microfluidic passage 14 is amplified due to the optofluidic lens effect on the photodetector 5. Due to the design of the test system 1 proposed by the invention, the signal intensity is increased by the lens effect as the first solution flows through the microfluidic passage 14. This signal amplification is very perceptible and can therefore be easily detected, as illustrated in FIG. 2, where I(AU) denotes the change in the intensity of the light signal.

The second micro-pump 10 is then activated in order to transport the other solution, preferably an enzyme solution, from the second bag 7 via the fluid line 12, check valve 9 and micro-pump 10 to the second nozzle 11 and from there to dispense it in the form of nanoliter drops into the sample application opening 13 of the microfluidic device 2. Due to capillary action, the solution is likewise drawn into the measuring region of the microfluidic device 3. Due to the presence of the first solution, in particular the chemiluminescent solution, the chemical or biochemical reaction of the two solutions takes place causing a light emission and a light signal is generated, in particular a chemiluminescence signal, which is measured in the measuring region. As soon as the light signal is detected, the micro-pump 10 is deactivated because the other solution, preferably an enzyme solution, extends as far as the outlet orifice of the second nozzle 11.

Based on a preferred embodiment, the microfluidic passage 14 is then rinsed, on the one hand to prevent a premature reaction of the next sample to be analyzed and on the other hand to prepare the nozzle 11 accordingly with the washing solution. To this end, a third micro-pump 10 is activated and the additional solution, in particular the washing solution, is transported from a third bag 7 with an interface 8 to the fluid line 12 via the check valve 9 and micro-pump 10 to the third nozzle 11 and from there dispensed in the form of nanoliter drops into the sample application opening 13 of the microfluidic device 3. By introducing the additional solution, in particular the washing solution, an additional volume of liquid is now present in the microfluidic passage 14 and the light signal, in particular the chemiluminescence signal, is shifted. As soon as this light signal shift is detected, in a particular chemiluminescence signal shift, the third micro-pump 10 is deactivated because the additional solution, in particular the washing solution, now also extends as far as the outlet end of the third nozzle 11.

Figure 1:
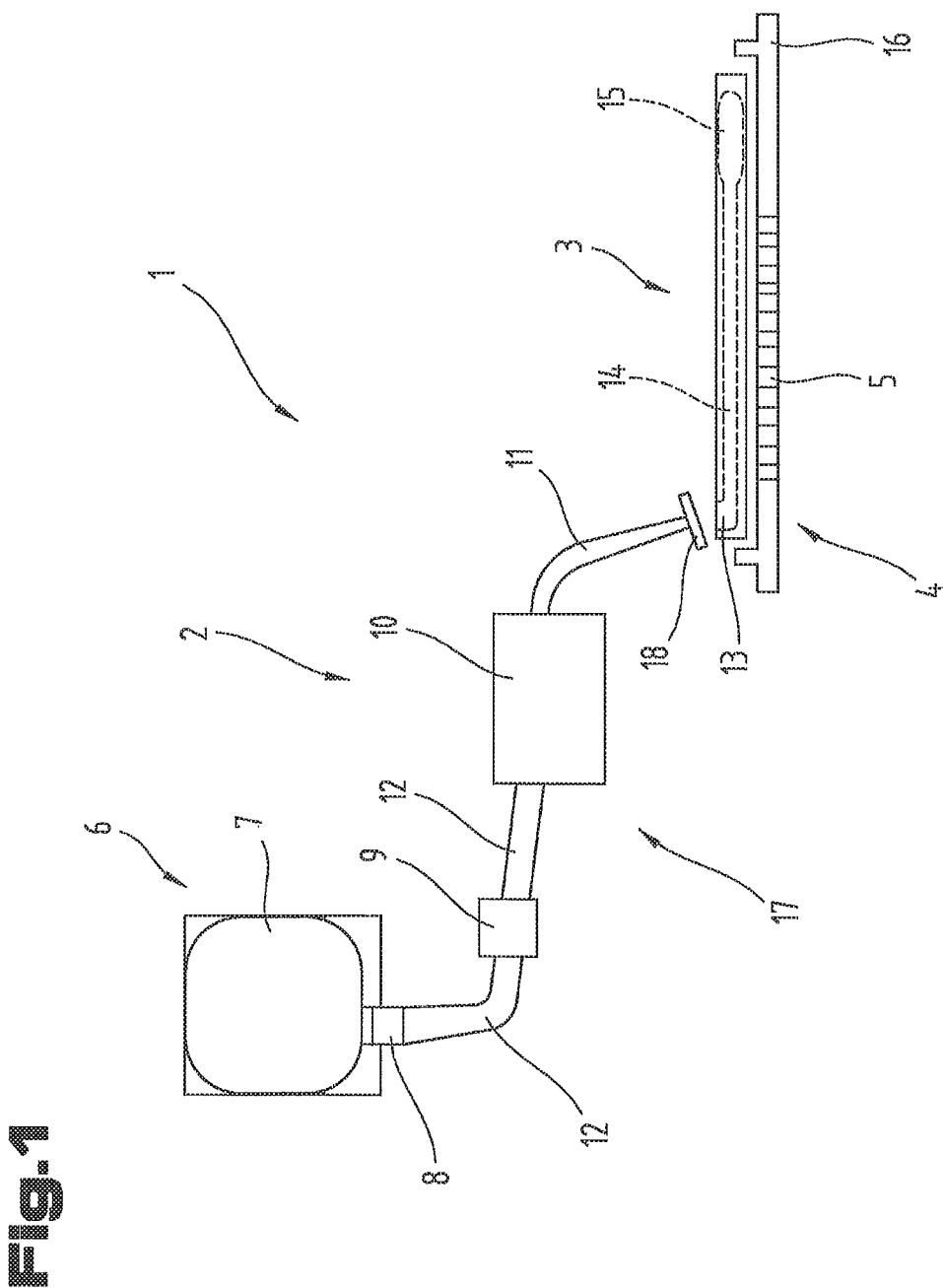
Figure 2:
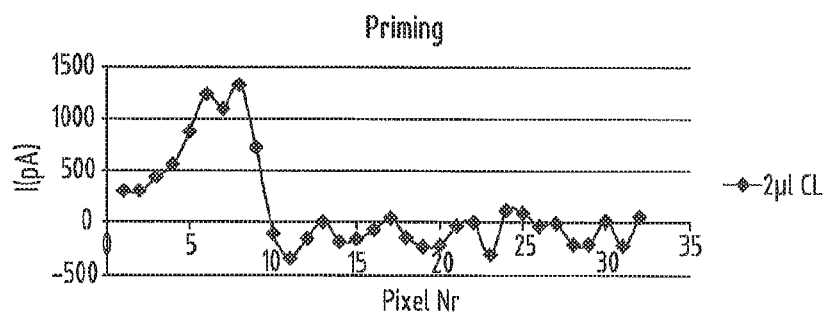
Figure 3:
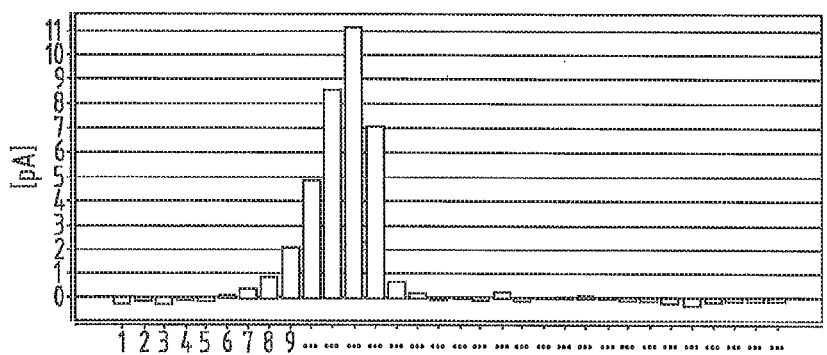
FIG. 3 illustrates the typical signal distribution of a chemiluminescence signal in the measuring region of the microfluidic passage 14 after the chemiluminescent solution has reacted with the enzyme solution, where [pA] denotes the y-axis photocurrent.
Figure 4:
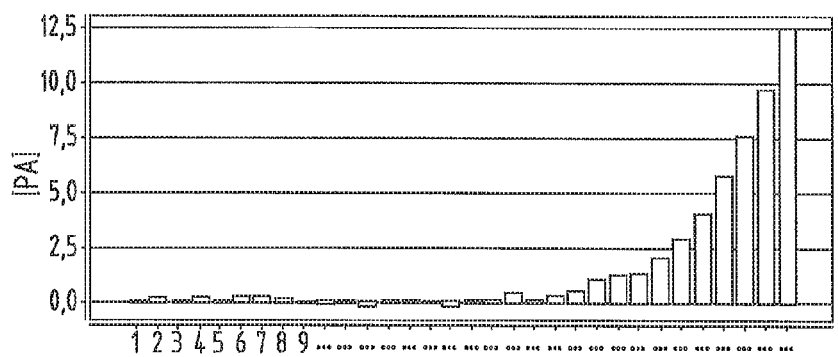
FIG. 4 illustrates the shift of the chemiluminescence signal after adding the washing solution.

At the latest when the third nozzle 11 has been filled as far as the end of the outlet orifice, the nozzles 11 can be closed by means of the sealing device 18. Naturally, the nozzles 11 may also be jointly or individually closed once the respective nozzle 11 has been filled, thereby preventing blockages of the nozzles 11 due to drying.

The nozzles 11 are now ready for the next test and volumes can be applied to the microfluidic device 3 with an accuracy of ±1 µl.

If the test system 1, in particular the dispensing system 2, is designed for applying volumes of 10 µl to 100 µl respectively, the bags 7 in the reservoir should have a holding capacity for ca. 50 tests, in other words ca. 0.5 ml to 5 ml.

When carrying out the next test, the sample to be analyzed is firstly introduced into the microfluidic device 3, and the sample can be pipetted or dropped directly into the sample application opening 13 or via a feeding device in the housing. The biological sample is then transported into the microfluidic passage 14, where target molecules of the biological sample react via specific binding sites with molecules immobilized in test sections of the measuring region. The other solution, preferably an enzyme solution, is then automatically added and thus drawn into the microfluidic passage 14. By adding the additional solution, in particular the washing solution, the surplus other solution, in particular enzyme solution, is removed in order to prevent any non-specific signals. Finally, the first solution, in particular the chemiluminescent solution, is automatically dispensed into the microfluidic device 3 and, due to a reaction with enzymes from the enzyme solution specifically bonded in the test sections, generates a light signal, in particular a chemiluminescence signal, which is measured by the photosensitive sensor 4 with a plurality of photodetectors 5 and it can be established by correlation with the test section in the measuring region what analyte is contained in the sample. As explained above, it is also possible to use other solutions which react to cause a change in color instead of the enzyme solution and chemiluminescent solution.

The light signal, in particular the chemiluminescence signal, is preferably measured by means of the photosensitive sensor 4 with several photodetectors 5 provided in the test system 1 but in an alternative embodiment may also be measured by means of an external sensor.

When testing the sample, it is necessary to document the measurement result. This being the case, an identity or identification feature may be provided on the microfluidic device 3 so that a direct correlation of the signal curve of the individual test sections can be transferred to a measurement protocol. Furthermore, different microfluidic devices 3 with different test sections may be used so that a code or configuration data of the test sections can also be stored in the identification feature. The feature is preferably provided in the form of a contactlessly operating reading device on the test system 1 and may be a 1D-code or 2D-code, although it would also be possible to provide an RFID feature. This reading device may be an optical 1D- or 2D detection sensor or an RFID transmitter and receiver unit, for example.

The embodiments illustrated as examples represent possible variants of the test system 1, and it should be pointed out at this stage that the invention is not specifically limited to the variants specifically illustrated, and instead the individual variants may be used in different combinations with one another and these possible variations lie within the reach of the person skilled in this technical field given the disclosed technical teaching. Accordingly, all conceivable variants which can be obtained by combining individual details of the variants described and illustrated are possible and fall within the scope of the invention.

For the sake of good order, finally, it should be pointed out that, in order to provide a clearer understanding of the structure of the test system 1, it and its constituent parts are illustrated to a certain extent out of scale and/or on an enlarged scale and/or on a reduced scale.

The objective underlying the independent inventive solutions may be found in the description.

LIST OF REFERENCE NUMBERS

1 Test system
2 Dispensing system
3 Microfluidic device
4 Photosensitive sensor
5 Photodetector
6 Container
7 Bag
8 Interface
9 Check valve
10 Micro-pump
11 Nozzle
12 Fluid line
13 Sample application opening
14 Microfluidic passage
15 Reservoir
16 Holder device
17 Dispenser unit
18 Sealing device

The invention claimed is:

1. Method of filling nozzles of a dispensing system of a test system comprising a dispensing system and a microfluidic device, which microfluidic device comprises at least one sample application opening and a microfluidic passage in which a measuring region is disposed, and the sample application opening is connected to the microfluidic passage, and the dispensing system comprises at least one container with at least one reservoir containing a solution, and the container is connected via a fluid line to at least one micro-pump, after which at least one nozzle is provided, the at least one nozzle being configured to dispense the solution into the sample application opening of the microfluidic device, the method comprising at least the following steps:
transporting the solution from the container via the nozzle of the dispensing system to the sample application opening of the microfluidic device via the micro-pump,
further transporting the solution into the measuring region of the microfluidic passage of the microfluidic device,
measuring a light signal in the measuring region of the microfluidic device via at least one photosensitive sensor with a plurality of photodetectors, and
deactivating the micro-pump when the light signal is detected and/or changes which indicates that the solutions have reached the measuring region of the microfluidic passage and hence are also present in the nozzles of the dispensing system which transports the liquids to the microfluidic device via the sample application opening.

2. Method according to claim 1, wherein the dispensing system comprises at least two containers containing solutions, the first container containing a first solution, and the second container containing another solution, and the first and the second containers are connected via a fluid line to at least one micro-pump, after which at least two nozzles are disposed, and a first nozzle of the at least two nozzles is used to dispense the first solution, and a second nozzle of the at least two nozzles is used to dispense the other solution into the sample application opening of the microfluidic device, the method comprising at least the following steps:
transporting the first solution and the other solution from the first container or the second container, respectively, via the first or the second nozzle, respectively, of the dispensing system to the sample application opening of the microfluidic device via the at least one micro-pump,
measuring a light signal caused by a reaction of the first solution and the other solution in the measuring region of the microfluidic device via at least one photosensitive sensor with a plurality of photodetectors, and
deactivating the at least one micro-pump when the light signal is detected.

3. Method according to claim 1, wherein the dispensing system comprises at least two containers containing solutions, the first container containing a first solution, and the second container containing another solution, and the first and the second containers are connected via a fluid line to at least one micro-pump, after which at least two nozzles are disposed, and a first nozzle of the at least two nozzles is used to dispense the first solution, and a second nozzle of the at least two nozzles is used to dispense the other solution into the sample application opening of the microfluidic device, the method comprising at least the following steps:
(a) the first solution is transported via the first nozzle to the sample application opening of the microfluidic device via the at least one micro-pump and is then sucked into the measuring region of the microfluidic device,
(b) a measurement is taken of the light signal in the measuring region of the microfluidic device via the photosensitive sensor with a plurality of photodetectors,
(c) the micro-pump is deactivated if there is a change in the light signal due to an optofluidic lens effect,
(d) the other solution is transported via the second nozzle to the sample application opening of the microfluidic device via the micro-pump and is then sucked into the measuring region of the microfluidic device,
(e) the light signal in the measuring region of the microfluidic device is detected via the photosensitive sensor with a plurality of photodetectors, and
(f) the micro-pump is deactivated when the light signal is detected.

4. Method according to claim 1, wherein the light signal is changed by an optofluidic lens effect as soon as the solution is transported into the microfluidic passage.

5. Method according to claim 1, wherein other steps are implemented, whereby
(a) an additional solution is transported via another nozzle to the sample application opening of the microfluidic device via the micro-pump and is then sucked into the measuring region of the microfluidic device,
(b) the shift of the previously measured light signal is measured in the measuring region of the microfluidic device via the photosensitive sensor with a plurality of photodetectors, and
(c) the micro-pump is deactivated when a light signal shift is detected.

6. Method according to claim 1, wherein the at least one nozzle has an outlet orifice which is closed via at least one sealing device after the micro-pump has been deactivated.

7. Method according to claim 1, wherein a stream of nanoliter drops of the respective solution is generated due to the combination of the micro-pump and the nozzle.

8. Method according to claim 1, wherein after filling the at least one nozzle of the dispensing system, a biological sample is introduced into the sample application opening and transported into the microfluidic passage where target molecules of the biological sample react via specific binding sites with molecules disposed in test sections of the measuring regions, and by adding the solutions from the dispensing system a chemical or biochemical reaction takes place generating a light emission and a light signal is generated which is detected via the photosensitive sensor with a plurality of photodetectors.

9. Test system, for a method according to claim 1, comprising at least one dispensing system, a microfluidic device and at least one photosensitive sensor with a plurality of photodetectors
which microfluidic device has a sample application opening and a microfluidic passage in which a measuring region is disposed, and the sample application opening is connected to the microfluidic passage and the microfluidic device is detachably disposed in a holder device of the test system so that the measuring region is disposed above the photodetectors of the photosensitive sensor,
and the dispensing system comprises at least one container with at least one reservoir containing a solution, and the container is connected via a fluid line to at least one micro-pump, after which at least one nozzle is provided and is configured to dispense the solution into the sample application opening of the microfluidic device and solutions are present in the nozzles of the dispensing system when a light signal is detected and/or changes in the measuring region of the microfluidic passage.

10. Test system according to claim 9, wherein the dispensing system comprises at least two containers containing solutions, and a first container of the at least two containers contains a first solution and a second container of the at least two containers contains another solution, and the first and the second containers are connected via a fluid line to the at least one micro-pump after which at least two nozzles are disposed, and a first nozzle of the at least two nozzles is used to dispense the first solution, and a second nozzle of the at least two nozzles is used to dispense the other solution into the sample application opening of the microfluidic device.

11. Test system according to claim 9, wherein the at least one container has an interface with a port to provide a connection to a standard luer cone of the fluid line.

12. Test system according to claim 9, wherein the at least one container is provided in the form of a collapsible bag.

13. Test system according to claim 9, wherein at least one check valve is disposed in the fluid line between the container and the micro-pump.

14. Test system according to claim 9, wherein at least one sealing device is disposed in the region of an outlet orifice of the at least one nozzle.

15. Test system according to claim 9, wherein the dispensing system comprises at least two dispenser units, and in the first dispenser unit at least one first container containing a first solution is disposed which is connected via a first fluid line to at least one first micro-pump and then to a first nozzle, and in the second dispenser unit at least one second container containing another solution is disposed which is likewise connected via a second fluid line to at least one second micro-pump and then to a second nozzle and optionally in a third dispenser unit at least one third container containing an additional solution is disposed which is likewise connected via a third fluid line to at least one third micro-pump and then to a third nozzle.

16. Test system according to claim 15, wherein in each dispenser unit the container is provided with an interface with a port to establish a connection to a standard luer cone and at least one check valve is disposed in the respective fluid line between the respective container and the respective micro-pump.

17. Test system according to claim 15, wherein the respective nozzles of adjacent dispenser units are disposed so that they dispense nanoliter drops of the respective solution into the same sample application opening of the microfluidic device.

18. Test system according to claim 9, wherein an outlet end of the at least one nozzle is disposed at a distance of 0.1 mm to 80 mm from the sample application opening of the microfluidic device.

* * * * *